United States Patent [19]

Hiltebrandt

[11] 4,063,796
[45] Dec. 20, 1977

[54] OPTICAL DEVICE FOR AN ENDOSCOPE WITH BELLOWS EXPANSION COMPENSATION MEANS

[75] Inventor: Siegfried Hiltebrandt, Knittlingen, Germany

[73] Assignee: Richard Wolf GmbH, Knittlingen, Germany

[21] Appl. No.: 698,899

[22] Filed: June 23, 1976

[30] Foreign Application Priority Data
June 25, 1975 Germany .................. 7520162[U]

[51] Int. Cl.² ............................................. G02B 7/00
[52] U.S. Cl. ........................................ 350/70; 128/4
[58] Field of Search ................ 350/69, 70, 78, 96 BC, 350/96 B; 356/241; 128/4-9

[56] References Cited
U.S. PATENT DOCUMENTS

| 2,453,862 | 11/1948 | Salisbury | 350/76 |
| 3,155,761 | 11/1964 | Rubens et al. | 356/241 |
| 3,417,745 | 12/1968 | Sheldon | 350/96 BC |
| 3,525,331 | 8/1970 | Mori | 350/96 BC |

Primary Examiner—Jon W. Henry
Attorney, Agent, or Firm—Kinzer, Plyer, Dorn & McEachran

[57] ABSTRACT

An optical device for an endoscope comprises inner and outer tubes of which the inner contains the optical system, a sleeve of wider internal diameter than the tubes, the sleeve being rigidly connected to the proximal end part of the outer tube and being connected to the inner tube, and means interposed in the connection between the inner tube and the sleeve for taking up relative longitudinal expansion therebetween.

1 Claim, 2 Drawing Figures

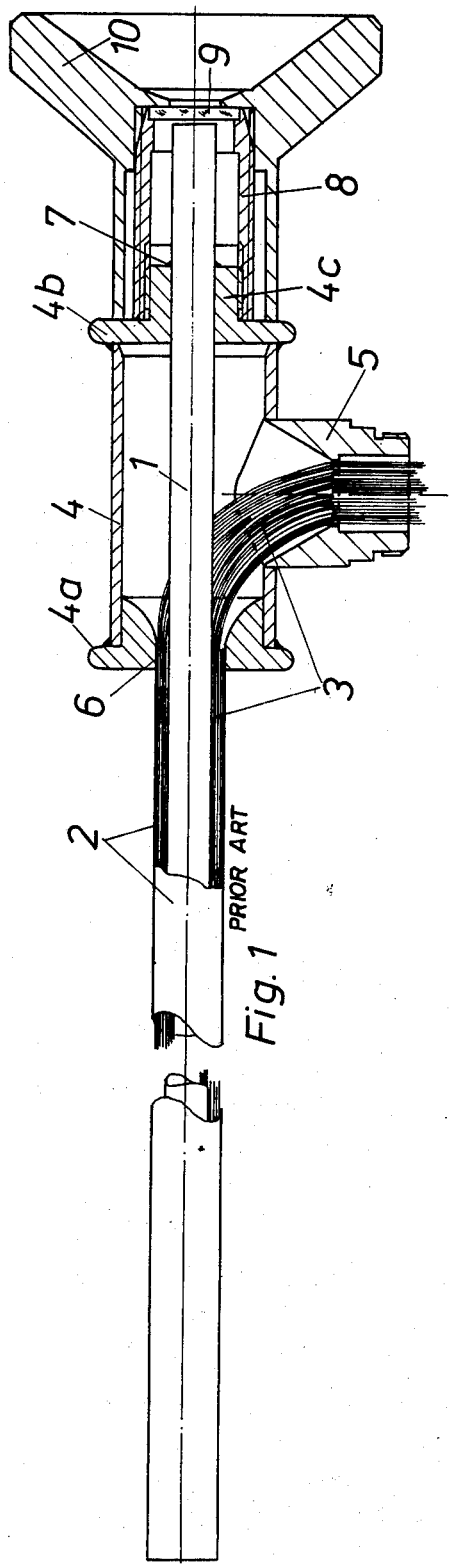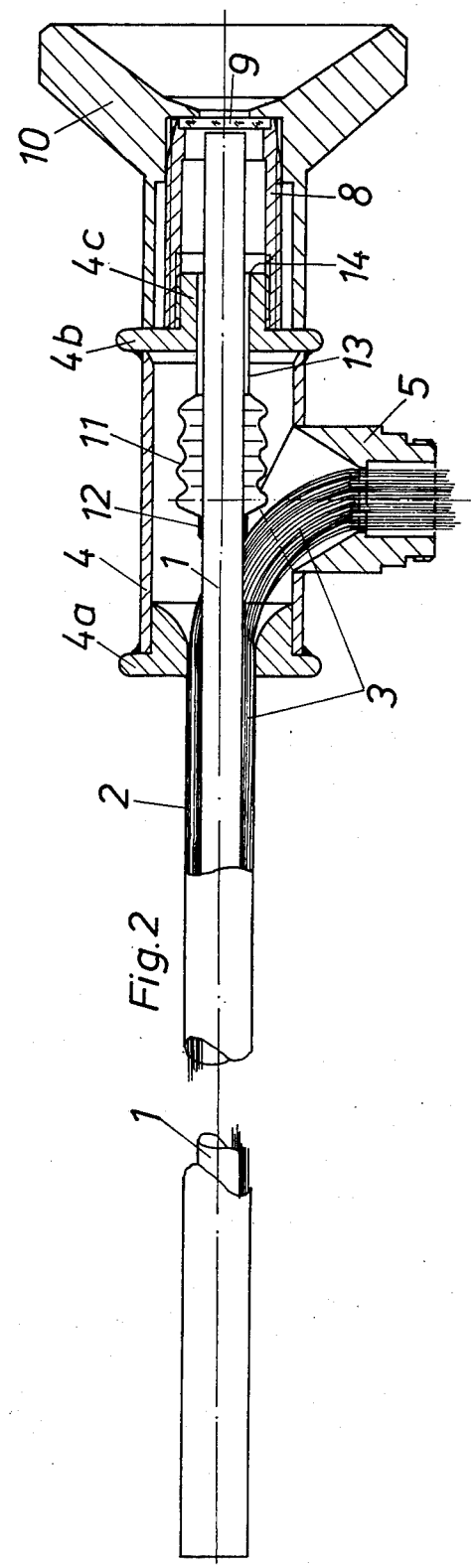

OPTICAL DEVICE FOR AN ENDOSCOPE WITH BELLOWS EXPANSION COMPENSATION MEANS

BACKGROUND OF THE INVENTION

1. Field of the Invention

The invention relates to an optical device for medical endoscopes or technical (engineering) endoscopes e.g. for examining visually the inside of an object such as a car engine, and more particularly to such an optical device of the kind comprising an inner tube which holds the optical system and is situated in an outer tube, the outer tube being rigidly connected at its proximal end part to a sleeve of enlarged internal diameter which is connected to an eyepiece and through which the inner tube passes.

2. Description of the Prior Art

In the known optical devices of the aforementioned kind of endoscopes, on the one hand the outer tube is rigidly connected to the distal part of the wide sleeve and on the other hand the inner tube is rigidly connected to the proximal part of the wide sleeve, e.g. by soldering. However, if for medical reasons sterilisation with superheated steam at 134° C has to be performed or, in the case of engineering endoscopes, if they have for example to be inserted through sparking-plug holes in order to examine the insides of the cylinders of engines while they are still hot, differing amounts of expansion occur between the widened sleeve connected to the outer tube and the inner tube, which is also rigidly connected to the sleeve. This difference in expansion sets up stresses which may give rise to fractures, particularly at the soldered joints.

The main object of the present invention is, therefore, to compensate for the difference in expansion of the metal parts of the optical device.

SUMMARY OF THE INVENTION

This object is achieved in accordance with the invention in an optical device of the kind initially described, be freely enclosing the inner tube, in the widened sleeve, in a member which takes up longitudinal expansion and which is connected at its distal end to the inner tube and is provided at its proximal end with an extension which is a clearance fit around the inner tube and is rigidly connected to the proximal part of the widened sleeve.

In this way it is possible for the widened sleeve, and the eyepiece, to expand freely relative to the inner tube which passes through it, by which means stresses, and the risk of fracture which they involve, are prevented, in particular at the soldered joints.

BRIEF DESCRIPTION OF THE DRAWINGS

FIG. 1 is an axial section through a known optical device for endoscopes with the distal part of the device being shown in side-view, and FIG. 2 is a similar axial section through an optical device constructed in accordance with the invention.

In the drawings the same reference characters are used to designate the same or similar parts.

DESCRIPTION OF THE PREFERRED EMBODIMENT

As shown in FIG. 1, an endoscopic optical device consists of a metal inner tube 1 which contains in a known way the optical system (i.e. lenses, dimming rings and so on for image transmission) (not shown) and which extends into a metal outer tube 2. The space between the inner and outer tubes 1 and 2 is used to accommodate a fibre light conductor 3 which encloses the inner tube at its centre to provide straight-ahead vision and eccentrically to provide lateral vision, so doing in a crescent shape. Alternatively, the space between the inner tube 1 and the outer tube 2 may be used to house electrical conductors which lead to a lamp at the distal end of the device. In the case of the optical device shown, the fibre light-conductor 3 is curved sideways out of the space between the tubes 1 and 2 into a metal sleeve 4 which is wider than the tube 2 and thence to a nipple 5 to which a light conductor from a light source can be connected. The fibres of the light-conductor are cemented into the nipple 5 and are ground flush with the latter at its outer end.

The proximal end part of the outer tube 2 is soldered at 6 to a flanged collar 4a associated with the sleeve 4, and the proximal part of the inner tube 1 is soldered at 7 into a flanged collar 4b at 7 having an externally threaded projection 4c. An eyepiece section 8, which has a transparent terminal disc 9 conveniently made of glass, is screwed onto the threaded projection 4c, and an eyepiece 10 itself is screwed onto the eyepiece section 8 by means of interengaging screw-threads. The optical device of FIG. 1 has the disadvantage that the soldered together metal parts 1, 2, 4 undergo different amounts of expansion, for example when heat sterilized, so that stresses and fractures may result.

FIG. 2 shows an optical device which is constructed to compensate for the differing longitudinal expansions in the soldered-together metal parts, 1, 2, 4 when being heat sterilized, thereby to substantially reduce or eliminate the stresses and fractures which may result in the device of FIG. 1. In FIG. 2 a bellows 11 is interposed between the inner tube and the distal end of the bellows 11 is soldered at 12 to the inner tube 1 in the sleeve 4, the bellows being provided at its proximal end with a cylindrical extension 13. This extension is a clearance fit around the inner tube 1 and is soldered at its proximal end, at 14, to the projection 4c of the flanged collar 4b.

Should differing amounts of expansion now occur in the widened sleeve 4 connected to the outer tube 2 and the inner tube 1 when heat sterilisation is taking place or when articles are being examined at high temperatures, the difference in expansion is taken up by the bellows 11 whereby internal stresses are compensated for and the possibility of fracture is eliminated.

Various modifications may be made without departing from the scope of the invention as defined in the appended claims. Thus any other components which take up expansion may be used instead of a bellows, e.g. telescopic tubes, elastic sleeves or the like.

I claim:

1. In an optical device for an endoscope, comprising an inner tube which holds an optical system and which extends into an outer tube having a proximal end region rigidly connected to a sleeve which is of enlarged internal diameter, said sleeve being connected to an eyepiece into which the inner tube also extends, the improvement comprising: means interposed between the inner tube and the sleeve for taking up relative longitudinal expansion therebetween, whereby to compensate for differing amounts of longitudinal expansion in the inner tube, the outer tube and the sleeve to reduce the possibility of stresses and fractures when the optical device is heated; said means comprising a bellows which extends around said inner tube, said bellows being connected at its distal end to the inner tube and being provided at its proximal end with an extension which has a clearance fit around the inner tube and is rigidly connected to a proximal part of the sleeve.

* * * * *